US006203430B1

(12) United States Patent
Walker et al.

(10) Patent No.: US 6,203,430 B1
(45) Date of Patent: Mar. 20, 2001

(54) ELECTRONIC AMUSEMENT DEVICE AND METHOD FOR ENHANCED SLOT MACHINE PLAY

(75) Inventors: Jay S. Walker, Ridgefield; James A. Jorasch, Stamford; Magdalena Mik, Greenwich, all of CT (US)

(73) Assignee: Walker Digital, LLC, Stamford, CT (US)

( * ) Notice: Subject to any disclaimer, the term of this patent is extended or adjusted under 35 U.S.C. 154(b) by 0 days.

(21) Appl. No.: 09/164,473

(22) Filed: Oct. 1, 1998

(51) Int. Cl.[7] ........................................ A63F 9/24
(52) U.S. Cl. ........................ 463/20; 463/16; 463/25; 273/26; 273/27; 273/143 R
(58) Field of Search .................... 463/16, 20, 25, 463/26, 27; 273/143 R

(56) References Cited

U.S. PATENT DOCUMENTS 4,184,683   1/1980   Hooker .
4,570,934   2/1986   Smyth .

(List continued on next page.)

FOREIGN PATENT DOCUMENTS

WO 98/19280   5/1998   (WO) .

OTHER PUBLICATIONS

The Game King, Casino Journal (http://www.casino center.com/journal/oct97/html/igt.html), Oct. 1997.
Marian Green, "The New Slot Market", International Gaming & Wagering Business, May 1998 at p. 1.
Melissa Cook, "The Best New Slots", Casino Player, Apr. 1998 at p. 44.
"Innovative Gaming Announces Nevada Approval of IGT Joint Venture Game—Bonus Streak", PR Newswire, May 14, 1997.
John Grochowski, "Royal is Worth Taking a Risk", Chicago Sun–Times, Apr. 5, 1998 at p. 18.
David Poole, "Letter from Charlotte: Vegas Perfect for Racing", Las Vegas Review–Journal, Jun. 22, 1997 at p. 2C.
"A New Generation", Casino Journal (http://www.casinocenter.com/journal/oct97/html/bally.html), Oct. 1997.
"The Interactive Experience", Casino Journal (http://www.casinocenter.com/jouranl/oct97/html/ac_coin.html), Oct. 1997.

*Primary Examiner*—Michael O'Neill
*Assistant Examiner*—Carmen D. White
(74) *Attorney, Agent, or Firm*—Steven M. Santisi; Dean P. Alderucci

(57) ABSTRACT

An electronic amusement device and a method for operating the device are disclosed. In accordance with one embodiment, a slot machine identifies a tracked symbol and initializes a running count representing active occurrences of the tracked symbol generated during a play session. During the session, the slot machine generates at least one outcome represented by a set of symbols and determines whether the outcome includes an occurrence of a tracked symbol. The slot machine adjusts the running count, increasing the running count to reflect occurrences of the tracked symbol and decreasing the running count to reflect expiration of occurrences of the tracked symbol. Once the running count reaches a predetermined level, the slot machine determines a bonus payout based on the running count.

49 Claims, 12 Drawing Sheets

U.S. PATENT DOCUMENTS

| | | |
|---|---|---|
| 4,669,731 | 6/1987 | Clarke . |
| 5,108,099 | 4/1992 | Smyth . |
| 5,123,649 | 6/1992 | Tiberio . |
| 5,178,390 | 1/1993 | Okada . |
| 5,370,399 | 12/1994 | Liverance . |
| 5,393,061 | 2/1995 | Manship et al. . |
| 5,449,173 | 9/1995 | Thomas et al. . |
| 5,559,312 | 9/1996 | Lucero . |
| 5,580,309 * | 12/1996 | Piechowiak et al. .................. 463/16 |
| 5,639,088 | 6/1997 | Schneider et al. . |
| 5,655,961 | 8/1997 | Acres et al. . |
| 5,695,402 | 12/1997 | Stupak . |
| 5,697,843 | 12/1997 | Manship et al. . |
| 5,702,304 | 12/1997 | Acres et al. . |
| 5,704,835 | 1/1998 | Dietz, II . |
| 5,720,662 | 2/1998 | Holmes, Jr. et al. . |
| 5,722,891 | 3/1998 | Inoue . |
| 5,741,183 | 4/1998 | Acres et al. . |
| 5,800,264 * | 9/1998 | Pascal et al. ............................ 463/16 |
| 5,833,538 * | 11/1998 | Weiss ..................................... 463/21 |
| 5,833,540 * | 11/1998 | Miodunski et al. ................... 463/42 |
| 5,910,048 * | 6/1999 | Feinberg ............................... 463/25 |
| 5,997,401 * | 12/1999 | Crawford .............................. 463/20 |
| 6,004,207 * | 12/1999 | Wilson, Jr. et al. ................... 463/20 |

* cited by examiner

400

| SYMBOL 410 | COUNT 412 |
|---|---|
| BELL | 12 |
| ORANGE | 29 |
| BAR | 2 |

420 — (row: BELL)
430 — (row: ORANGE)
440 — (row: BAR)

FIG. 4A

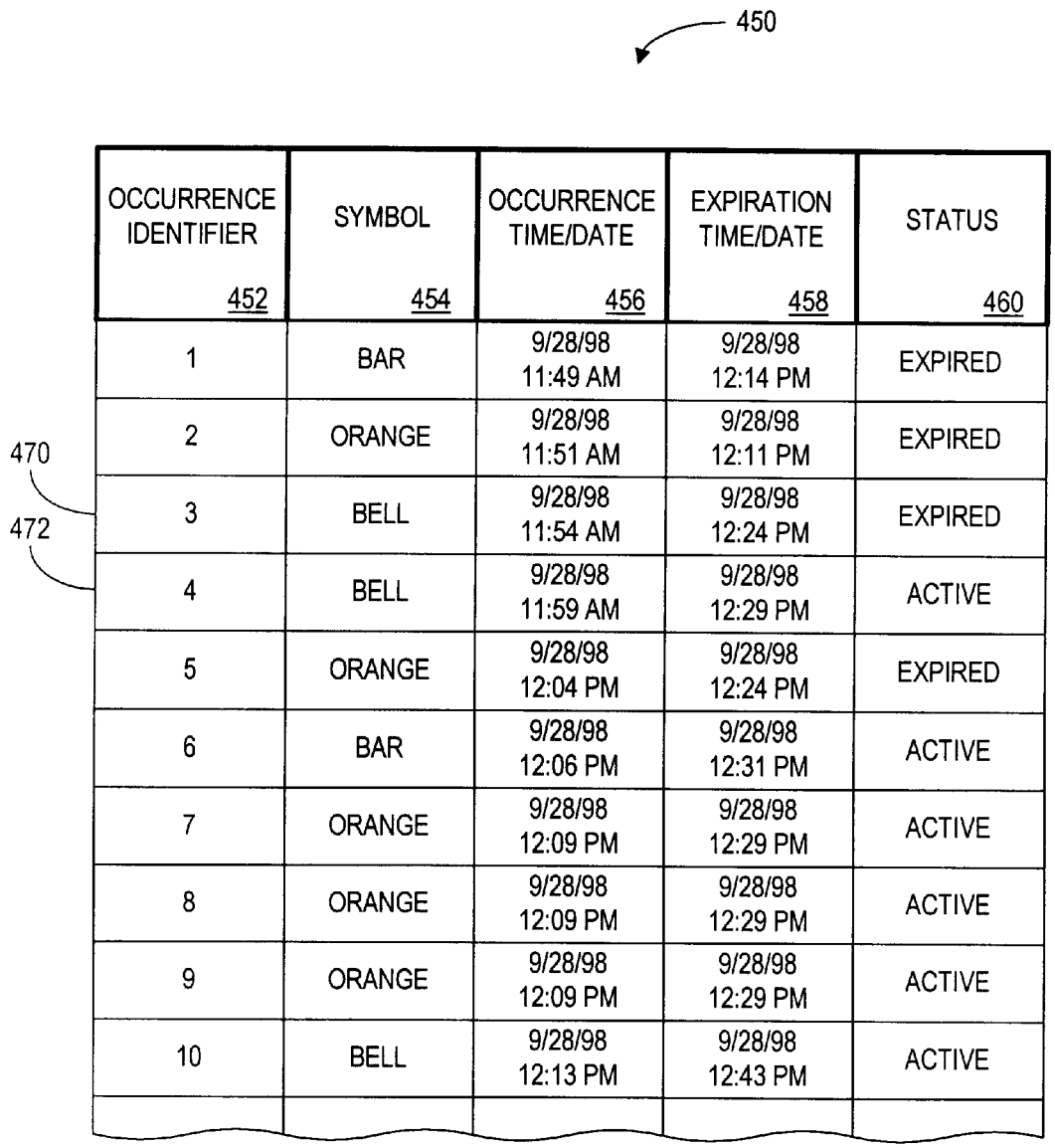
| OCCURRENCE IDENTIFIER 452 | SYMBOL 454 | OCCURRENCE TIME/DATE 456 | EXPIRATION TIME/DATE 458 | STATUS 460 |
|---|---|---|---|---|
| 1 | BAR | 9/28/98 11:49 AM | 9/28/98 12:14 PM | EXPIRED |
| 2 | ORANGE | 9/28/98 11:51 AM | 9/28/98 12:11 PM | EXPIRED |
| 3 | BELL | 9/28/98 11:54 AM | 9/28/98 12:24 PM | EXPIRED |
| 4 | BELL | 9/28/98 11:59 AM | 9/28/98 12:29 PM | ACTIVE |
| 5 | ORANGE | 9/28/98 12:04 PM | 9/28/98 12:24 PM | EXPIRED |
| 6 | BAR | 9/28/98 12:06 PM | 9/28/98 12:31 PM | ACTIVE |
| 7 | ORANGE | 9/28/98 12:09 PM | 9/28/98 12:29 PM | ACTIVE |
| 8 | ORANGE | 9/28/98 12:09 PM | 9/28/98 12:29 PM | ACTIVE |
| 9 | ORANGE | 9/28/98 12:09 PM | 9/28/98 12:29 PM | ACTIVE |
| 10 | BELL | 9/28/98 12:13 PM | 9/28/98 12:43 PM | ACTIVE |
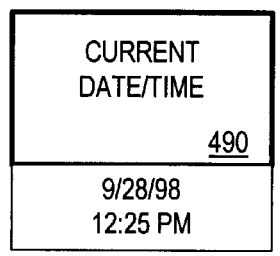
| CURRENT DATE/TIME 490 |
|---|
| 9/28/98 12:25 PM |
FIG. 4B

|  | PAYOUTS | | |
| --- | --- | --- | --- |
| OUTCOME 502 | 1 COIN WAGERED 504 | 2 COINS WAGERED 506 | 3 COINS WAGERED 508 |
| NON-WINNING COMBINATION | 0 | 0 | 0 |
| CHERRY/ANY/ANY | 2 | 4 | 6 |
| ANY/ANY/CHERRY | 2 | 4 | 6 |
| CHERRY/CHERRY/ANY | 5 | 10 | 15 |
| ANY/CHERRY/CHERRY | 5 | 10 | 15 |
| CHERRY/ANY/CHERRY | 5 | 10 | 15 |
| CHERRY/CHERRY/CHERRY | 20 | 40 | 60 |
| BAR/ORANGE/ORANGE | 10 | 20 | 30 |
| ORANGE/ORANGE/BAR | 10 | 20 | 30 |
| ORANGE/ORANGE/ORANGE | 20 | 40 | 60 |
| BAR/PLUM/PLUM | 14 | 28 | 42 |
| PLUM/PLUM/BAR | 14 | 28 | 42 |
| PLUM/PLUM/PLUM | 20 | 40 | 60 |
| BAR/BELL/BELL | 18 | 36 | 54 |
| BELL/BELL/BAR | 18 | 36 | 54 |
| BELL/BELL/BELL | 20 | 40 | 60 |
| BAR/BAR/BAR | 50 | 100 | 150 |
| 7/7/7 | 100 | 200 | 600 |

FIG. 5

PRIOR ART

600 ↙

| OUTCOME 602 | RANDOM NUMBER 604 | EXPECTED HITS PER CYCLE 606 |
|---|---|---|
| NONWINNING COMBINATION | 1-8570 | 8570 |
| CHERRY/ANY/ANY | 8571-9250 | 680 |
| ANY/ANY/CHERRY | 9251-9930 | 680 |
| CHERRY/CHERRY/ANY | 9931-10130 | 200 |
| ANY/CHERRY/CHERRY | 10131-10330 | 200 |
| CHERRY/ANY/CHERRY | 10331-10398 | 68 |
| CHERRY/CHERRY/CHERRY | 10399-10418 | 20 |
| BAR/ORANGE/ORANGE | 10419-10460 | 42 |
| ORANGE/ORANGE/BAR | 10461-10466 | 6 |
| ORANGE/ORANGE/ORANGE | 10467-10508 | 42 |
| BAR/PLUM/PLUM | 10509-10528 | 20 |
| PLUM/PLUM/BAR | 10529-10533 | 5 |
| PLUM/PLUM/PLUM | 10534-10583 | 50 |
| BAR/BELL/BELL | 10584-10587 | 4 |
| BELL/BELL/BAR | 10588-10607 | 20 |
| BELL/BELL/BELL | 10608-10627 | 20 |
| BAR/BAR/BAR | 10628-10647 | 20 |
| 7/7/7 | 10648 | 1 |

616 points to the CHERRY/ANY/CHERRY and ANY/CHERRY/CHERRY rows.

FIG. 6

PRIOR ART

| OUTCOME IDENTIFIER 702 | REEL 1 704 | REEL2 706 | REEL3 708 |
|---|---|---|---|
| 1 | BAR | BAR | PLUM |
| 2 | CHERRY | BAR | BAR |
| 3 | LEMON | ORANGE | ORANGE |
| 4 | BELL | ORANGE | BAR |
| 5 | BAR | 7 | 7 |
| 6 | BELL | ORANGE | LEMON |
| ... | ... | ... | ... |
| 45 | BAR | 7 | CHERRY |
| 46 | CHERRY | LEMON | 7 |
| 47 | PLUM | PLUM | ORANGE |
| 48 | 7 | BAR | PLUM |
| 49 | CHERRY | BELL | BAR |
| 50 | PLUM | BAR | 7 |

ELECTRONIC AMUSEMENT DEVICE AND METHOD FOR ENHANCED SLOT MACHINE PLAY

BACKGROUND OF THE INVENTION

1. Field of the Invention

The present invention relates generally to electronic amusement devices and more particularly to an electronic amusement device such as a slot machine having the ability to determine a bonus payout based on a running count of tracked symbol occurrences.

2. Background of the Invention

Modern casinos offer players a wide variety of game alternatives, including table games such as craps, blackjack and poker. Slot machines, however, constitute the major source of profits for casinos. Casinos therefore constantly strive to increase the attractiveness and playability of slot machines in ways that attract and retain players.

More particularly, it is of substantial value to a casino to encourage lengthier and faster play sessions at slot machines. When a player terminates play and walks away from a slot machine, that machine often goes unused for some period of time until a new player initiates play, thereby reducing revenue from that slot machine. Further, the speed with which an active player operates a machine has a direct bearing on the profit of a machine; the faster a slot machine is played, the greater the profit that machine will generate for its owner.

One method that has been used to motivate increased play of slot machines is to generate bonus payouts dependent on cumulative effects of plays. For example, several reel slot machines manufactured by International Game Technology ("IGT") provide bonuses for the cumulative effects of spins. The game "Red, White and Blue Racing 7s" is representative of "racing" types of games, featuring a race based on a number of reel symbols obtained within a given time period. The three colors of the reel symbol "7" appear on the reels with different frequencies. When a "7" comes up on a reel, a racing character "7" of the same color advances on an animated track. When a racing character crosses the finish line, the player receives a bonus, with higher bonuses for the symbol colors of lower frequency.

Another example of a slot machine "racing" game is known wherein a group of slot machines are linked to five race cars. The cars move down a track every time a certain symbol comes up on one of the reels. If a car proceeds far enough within either a three and one-half minute or fifty-two spin period, it wins.

Slot machine racing games, such as the Red, White and Blue Racing 7s and the auto race games described above, encourage an increased rate of play. However, the excitement and the motivation last only for the limited period of the race. When the race ends, all player investment in the racing aspects of the game are lost, and the player may be motivated to cease play and search out another game.

In contrast to the racing games described above, another set of games uses accumulated reel spins to adjust different types of counting mechanisms. In such games, when a particular goal is met (e.g., a particular quantity of symbols is accumulated) a bonus is awarded.

The game "Double Diamond Mine" by IGT operates to allow players to collect diamond symbols from the three slot machine reels. The diamonds from each reel are counted and displayed by separate graphical counters. When a graphical counter indicates that it is "full," it is emptied and the player wins a bonus. Any accumulated diamonds remain in the other two graphical counters, so a player who wins a bonus still has some equity to protect by continuing to play.

In the games described above, casino operators are constrained in the amount of money that they can offer for the achievement of the bonuses because there is an inverse relationship between the payout amount and the odds of achieving the bonus payout. In order to make it economically feasible to offer a relatively high payout, the casino must set the odds for achieving the bonus payout relatively low, thereby discouraging players who "never seem to get close" to achieving a bonus. The casinos can increase the probability of winning a bonus payout, but only by decreasing the bonus payout amount, thereby significantly decreasing the player's motivation to remain at the machine.

In the IGT game "Wild Cherry Pie," whenever a Wild Cherry Pie symbol appears in the reel slot machine window—even if it's not on the payline—a cherry is added to a pie under construction on a display screen. The player wins a bonus when sufficient Wild Cherry Pie symbols have been accumulated to complete a section of the pie.

In another example of a cumulative bonus symbol type of game, AC Coin & Slot Service Company developed a series of games in which there was a time period during which a player attempted to accumulate a number of reel symbol outcomes. Three bonus payouts were provided at ten, fifteen and twenty-five coins, respectively. Each reel of the slot machine included one or more special symbols, the occurrence of which advanced the player closer to one of the three bonus levels. Upon the completion of a one-hundred second time period, the bonus session ended and the player result (i.e. the number of special reel symbols accumulated) was compared to the totals required to obtain each bonus level. Any bonus earned was paid out, and any accumulated special reel symbols were then zeroed out.

In the public-domain, Windows™-based slot machine game, "Power Play Slots," players' Power-Play symbols occurring on a payout line are 'collected' to add 10% to a power meter. A bonus is provided for reaching the top of the power meter. The occurrence of a Power Drain symbol voids any Power-Play symbols visible, and results in the loss of fifty percent of the accumulated power. Such a sizable setback is very discouraging to a player and may prompt the player to leave the machine.

In another public-domain, Windows™-based slot machine game, "Wild Wizard Slots" by Ultisoft, the letters B, O, and X are included amongst the reel symbols. As the game is played, each letter is accumulated until its individual count goes over seven; then it is reset to zero. If the total for all three symbols reaches twenty, the player wins the bonus pool. If it reaches 21, the player wins seven times the bonus pool. After either bonus is won, the total resets to zero.

In a three reel slot machine named "X Factor," Power Point symbols are provided on each reel which function to provide a bonus multiplier. Hence the name X Factor, where the X represents the earned multiplier. The bonus multiplier increases with continued appearances of Power Points, until a conventional payout is earned. The payout is multiplied by the bonus multiplier effective at that time, and the bonus multiplier is reset to zero.

These games all suffer from several shared disadvantages. First, the games do not accumulate symbols in a manner that maintains a constant state of motivation for the player to continue play. Each game presents its own periods of quiet time during which a player may be motivated to cease play. For example, the Double Diamond Mine, Wild Wizard Slots, and Wild Cherry Pie games have periods where bonuses are awarded, groups of bonus symbols are cancelled out, and bonus play may temporarily decline. With Power Play Slots, the accumulation of symbols takes a substantial setback every time a Power Drain symbol is hit, and drops to zero when a bonus is awarded. In the AC Coin & Slot Service Company games, accumulated bonus symbols are zeroed out every one hundred seconds. In the X Factor game, the bonus multiplier is cancelled out once it hits.

It would be highly desirable to provide such a slot machine, where a player is motivated, on a consistent and ongoing basis, to prolong session play so as to avoid losing accumulated credits. Such a game would preferably avoid the pitfalls of the prior art, particularly that of permitting lulls or quiescent periods where it appears that game play can be terminated without a significant loss of accumulated credits.

SUMMARY OF THE INVENTION

An object of the present invention is to provide an improved method and apparatus for determining a bonus payout based on a running count of tracked symbol occurrences. An advantage of the present invention for a casino operator is that it sustains the attention of slot machine players for a longer time, thereby increasing the average playing time for a slot machine. Another advantage of the present invention for a casino operator is that it encourages faster slot machine play by players using the device. An advantage of the present invention for a slot machine player is that it increases the excitement, anticipation and enjoyment of playing a slot machine.

In accordance with the present invention, an electronic amusement device and method is disclosed for directing a slot machine to process a bonus payout based on a running count of tracked symbol occurrences. The method includes the steps of identifying at least one tracked symbol and initializing a running count. The running count represents a number of occurrences of the tracked symbol, for example, during a particular time period or throughout a number plays of the slot machine.

The method also includes the step of generating an outcome represented by a set of symbols. The method further includes the step of determining an occurrence of any of the identified tracked symbols. The running count is adjusted accordingly, including increasing the running count to reflect occurrences of one of the tracked symbols and decreasing the running count to reflect expiration of occurrences of one of the tracked symbols. According to the method, a bonus payout is determined based on the running count.

BRIEF DESCRIPTION OF THE DRAWINGS

These and other objects, features and advantages of the invention will be understood from a consideration of the following description of the invention, in which:

FIG. 4A is a table showing components of the tracked symbol table of FIG. 3;

FIG. 4B is a table showing components of the occurrence table of FIG. 3;

FIG. 5 is a table showing components of the payout table of FIG. 3;

FIG. 6 is a table showing components of the probability table of FIG. 3;

FIG. 7 is a table showing components of the outcome table of FIG. 3;

DETAILED DESCRIPTION OF THE INVENTION

Slot machines, including conventional reel slot machines, video poker, video keno and video blackjack machines, are generally among the most profitable casino games. Casino operators can capture the interest of slot players by offering a bonus payout in addition to a traditional payout. By determining the bonus payout based on aggregated results of multiple plays during a gaming session, casino operators can encourage slot players to increase the average duration of their sessions. Further, because the bonus payout is based on multiple plays, such a bonus increases the anticipation, entertainment and excitement of a slot player.

The present invention is directed to an electronic gaming device and a method for operating an electronic gaming device to determine whether a number of occurrences of a tracked symbol during a session of slot play is sufficient to provide a bonus payout. The present invention maintains a running count of tracked symbols that have occurred, without expiring, during a gaming session, and determines a bonus payout when the running count reaches or surpasses a predetermined amount.

According to the present invention, a player begins a gaming session at a slot machine. During the session, the player plays a number of games, and generates an outcome for each game. Each outcome is represented by a set of symbols.

The slot machine identifies at least one tracked symbol, and throughout the session, the slot machine maintains a running count of the number of times the tracked symbol occurs in a generated outcome. In one embodiment, the running count may represent the number of times a specific symbol occurs in generated outcomes. In an alternate embodiment, the running count may represent the number of times any tracked symbol occurs in generated outcomes.

Although each occurrence of a tracked symbol causes the running count to be increased, an expiration condition is associated with each occurrence of a tracked symbol defining the condition under which the occurrence expires. Typically, an expiration condition is defined as a function of time or as a function of a number of plays. Upon the satisfaction of an expiration condition, the running count is decreased to reflect the expiration of an occurrence.

The preferred embodiment will be further described with reference to a client-server architecture in which much of the processing is performed by the networked gaming device. Of course, one skilled in the art will recognize various alternate embodiments that are consistent with the spirit and scope of the present invention, including without limitation performing the processing steps at the slot server.

Apparatus Architecture

Figure 1:
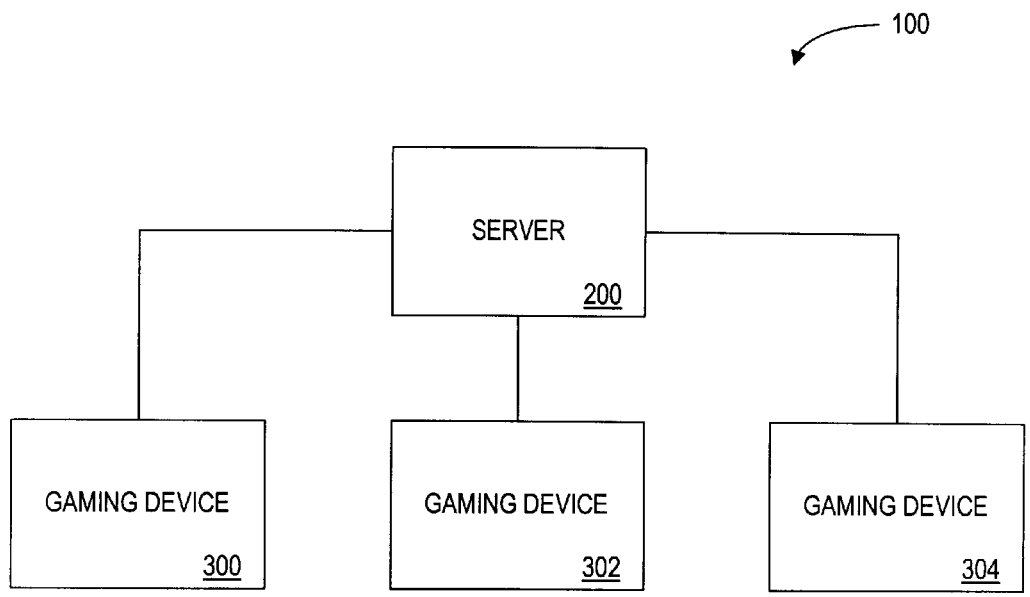
FIG. 1 is a block diagram illustrating a system for implementing the present invention.

The apparatus architecture of an exemplary embodiment of the present invention will now be discussed with reference to FIGS. 1–3. Referring to FIG. 1, there is shown a block diagram of a slot network 100. Network 100 includes a slot machine server 200 (hereinafter referred to as "server") that is linked to and communicates with networked gaming devices or slot machines 300, 302 and 304. Although three gaming devices are shown, a person of ordinary skill in the art will appreciate that any number of networked gaming devices could be linked to and in communication with server 200.

Figure 2:
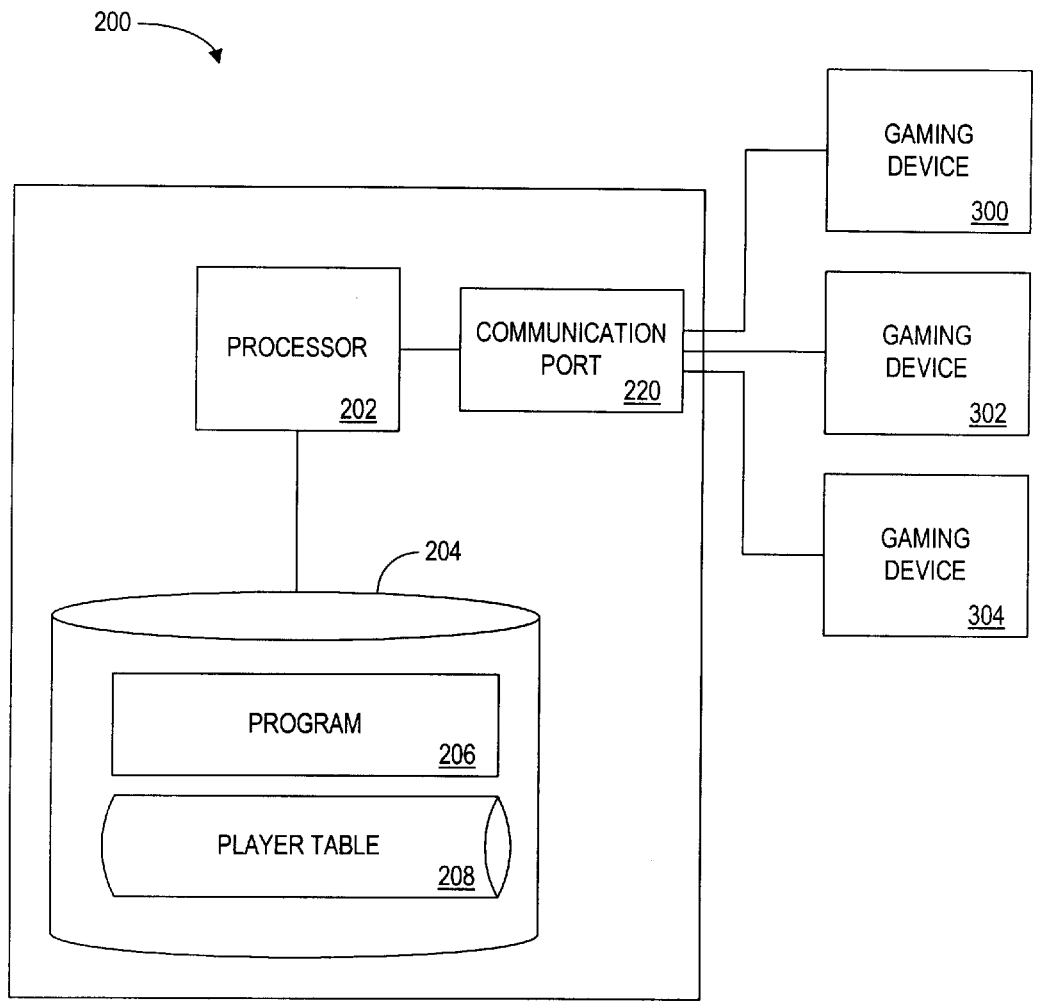
FIG. 2 is a block diagram of a slot server constructed in accordance with the present invention.

Referring now to FIG. 2, the architecture of slot machine server 200 is illustrated. In addition to conventional server components, server 200 includes a processor 202, a storage device 204 and a communication port 220. Communication port 220 enables server 200 to communicate with gaming devices 300, 302 and 304. Storage device 204 comprises an appropriate combination of magnetic and optical memory, such as disk drive memory, and semiconductor memory such as random access memory and read only memory. Storage device 204 contains program 206 and player table 208 for controlling server 200 in accordance with the present invention.

Figure 3A:
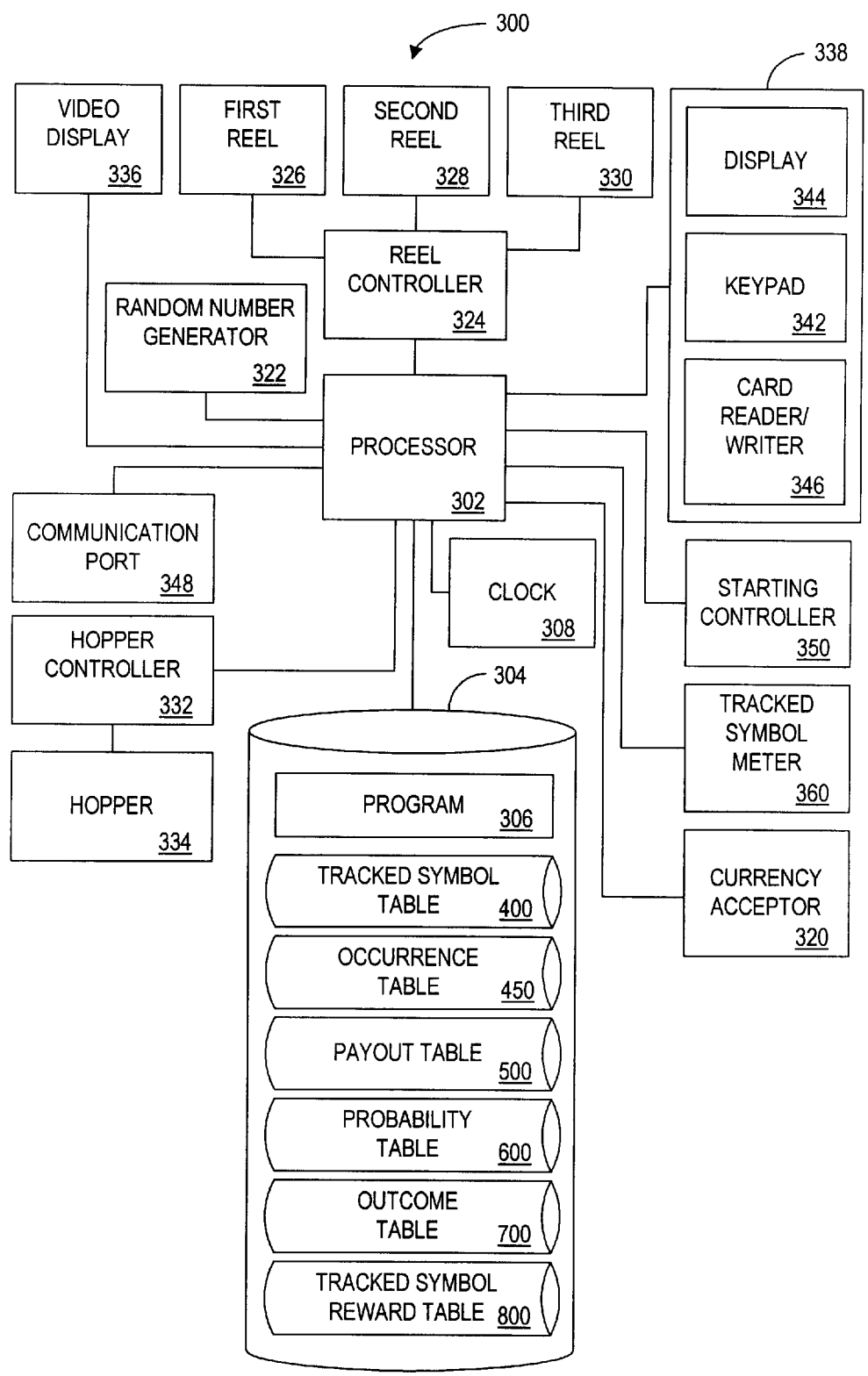
FIG. 3A is a block diagram of an electronic gaming device constructed in accordance with the present invention.

Referring now to FIG. 3A, the architecture of slot machine 300 is illustrated. Slot machine 300, which is substantially similar to slot machines 302 and 304, is controlled by processor 302 and communicates with slot server 200 via communication port 348. Processor 302 is connected to storage device 304 which stores program instructions and data for operating slot machine 300 in accordance with the present invention. Specifically, storage device 304 stores tracked symbol table 400, occurrence table 450, payout table 500, probability table 600, outcome table 700 and tracked symbol reward table 800, described more fully with reference to FIGS. 4A–8, respectively. Storage device 304 further stores program 306 which preferably includes instructions for conducting a game of chance and instructions for implementing the method of determining the bonus payout, as described more completely with reference to FIG. 9.

Further connected to processor 302 are a clock 308, a player card tracking device 338, a random number generator 322, a reel controller 324 for controlling reels 326, 328 and 330, a hopper controller 332 having an associated hopper 334, a currency acceptor 320, a video display 336 and a tracked symbol meter 360. It should be noted that video display 336 may display information which may serve as an adequate substitute for tracked symbol meter 360 as well as for reels 326, 328 and 330.

As illustrated, slot machine 300 comprises many conventional components. The non-conventional components of slot machine 300 include the program instructions and data stored in storage device 304 and the tracked symbol meter 360. For purposes of better illustrating the invention, conventional components, well known to those skilled in the art, are described only briefly. Although the present embodiment of the invention is described as implemented with physical components, the invention applies equally well to and includes software embodiments such as would be implemented on the Internet and other computer data networks.

Processor 302 may be embodied as one or more well known processing units, for example a Pentium class CPU manufactured by Intel Corp., or the like. Data storage device 304 comprises an appropriate combination of magnetic and optical memory, such as disk drive memory, and semiconductor memory such as random access memory and read only memory. In addition to the program instructions and data shown in FIG. 3, storage device 304 stores appropriate operating system and control software (not shown), functional to operate gaming device 300 in the manner described below. Random number generator 322 comprises one of many well known random or pseudo-random number generators suitable for use in a gaming device.

Currency acceptor 320 is operative to receive one or more coins or bills, and to transmit an appropriate value signal to processor 302. Hopper controller 332, and hopper 334 connected thereto, are operative under the control of processor 302 to dispense coins to a player. Starting controller 350 comprises a player-operated device such as a handle or button for initiating the play of a game.

Player card tracking device 338 comprises a player tracking interface including a card reader/writer 346 for receiving a player tracking card (not shown), a display 344 for communicating messages to the player, and a keypad 342 for receiving player input such as a player identifier.

Figure 3B:
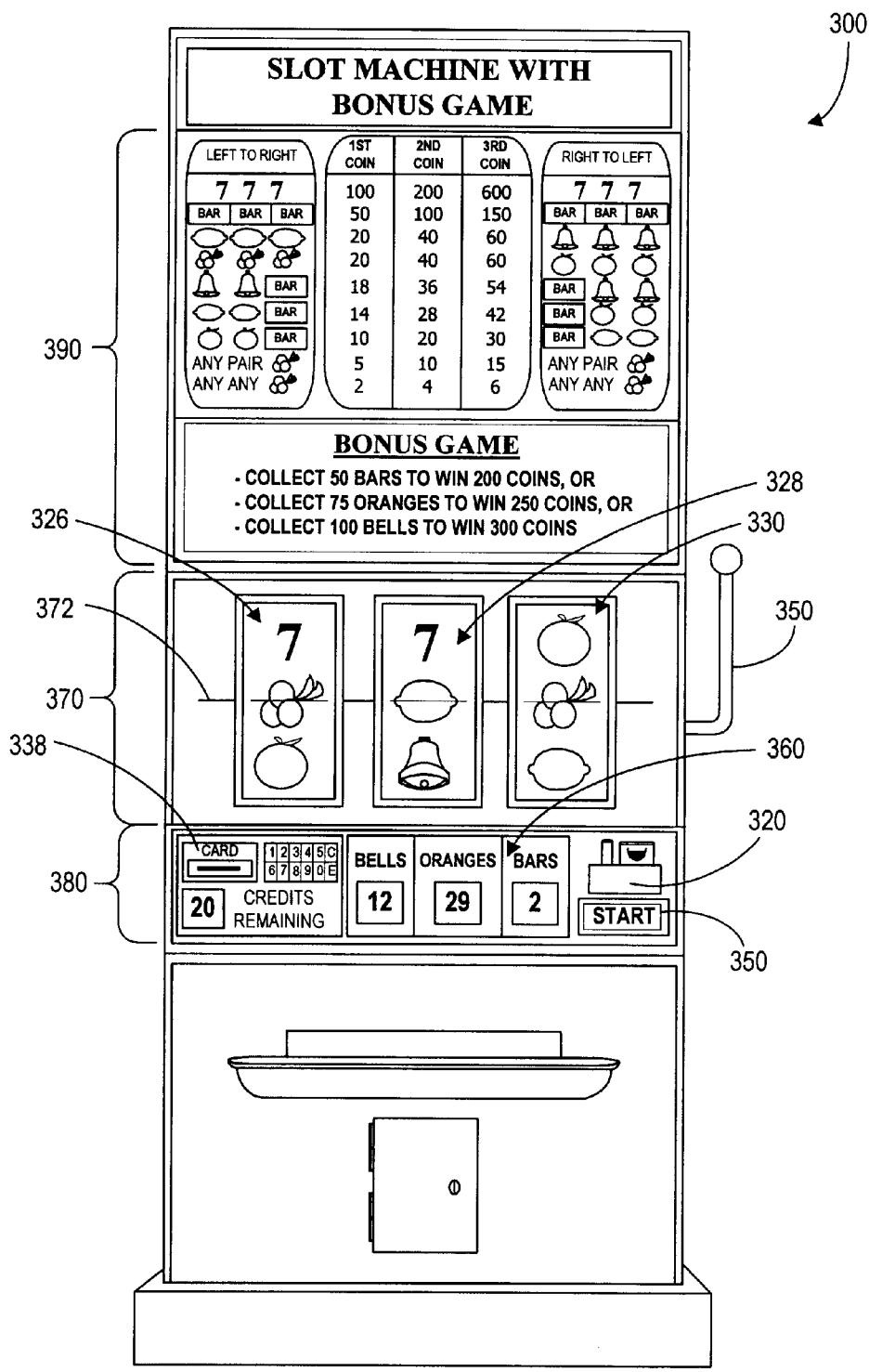
FIG. 3B is a plan view of the electronic gaming device of FIG. 3A.

Referring now to FIG. 3B, a front plan view is shown of slot machine 300 of the present invention which, for purposes of discussion, is generally divided into three sections: a central panel 370, a lower panel 380, and an upper panel 390. Central panel 370 includes the display of first reel 326, second reel 328, and third reel 330. Each of these reels is configured to display the symbols printed on an associated reel strip. The reels may be mechanical in nature, or electronically represented with outputs shown on conventional electronic displays, such as a liquid crystal display ("LCD"). Central panel 370 includes a payline 372 that indicates the symbols of a resultant outcome. Central panel 370 further includes starting controller 350, in the form of a handle.

Lower panel 380 houses player tracking device 338. To the right of player tracking device 338 is tracked symbol meter 360 which indicates the number of tracked symbols which have been accumulated by the player. On the right portion of lower panel 380 is currency acceptor 320 and starting controller 350.

Upper panel 390 includes a display showing the contents of payout table 500 which describes all possible payouts for the slot machine, the details of which are discussed with respect to FIG. 5. The information is typically printed in bright colors and may be back-lit for easier viewing. Upper panel 390 also includes a display showing the requirements and payouts of the bonus game.

Data Tables

Referring now to FIG. 4A, there are illustrated three representative records of an exemplary tracked symbol table 400. As illustrated, each record of tracked symbol table 400 represents the progress of a player toward achieving a bonus associated with a tracked symbol. Each record of tracked symbol table 400 includes a symbol 410 and a count 412. Symbol field 410 identifies the tracked symbol associated with the record, and running count field 412 identifies the number of non-expired occurrences of the symbol generated during a session. Accordingly records 420, 430 and 440 of tracked symbol table 400 show that during the current session of play, a player has an active total of 12 bell symbols, 29 orange symbols and 2 bar symbols, respectively. The displayed running count for each tracked symbol is periodically adjusted to account for expired occurrences of tracked symbols.

Referring now to FIG. 4B, there are illustrated ten representative records of an exemplary occurrence table 450. Each record of occurrence table 450 represents a single occurrence of a tracked symbol generated during a session. Each record of occurrence table 450 includes occurrence identifier field 452 which uniquely identifies a record. Symbol field 454 identifies the tracked symbol associated with the record.

The time and date that the symbol was generated is stored in occurrence time/date field 456, and time at which the occurrence expires is stored in expiration time/date field 458. Although the expiration time/date is illustrated as an expiration condition, other expiration conditions are also possible, such as number of plays. As illustrated by the records of occurrence table 450, ORANGE symbols expire twenty minutes after occurring, BAR symbols expire twenty-five minutes after occurring and BELL symbols expire thirty minutes after occurring. Although the exemplary records reflect expiration periods that are based on the associated tracked symbol, in an alternate embodiment of the present invention, random expiration periods could be assigned for every occurrence.

Status field 460 represents the status of the occurrence represented by a record. Status field 460 can store an indication of "ACTIVE" or "EXPIRED." If status field 460 contains "ACTIVE," the occurrence is included in the running count for the associated symbol. If status field 460 contains "EXPIRED," the occurrence of the symbol is not included in the running count. Assuming that clock 308 generates the current date/time of Sep. 28, 1998 12:25 pm, as illustrated by reference numeral 490, records 470 and 472 illustrate the use of status field 460. As shown, the occurrence represented by record 470 expired at 12:24 pm, one minute prior to the current date/time. Accordingly, status field 460 of record 470 is set to "EXPIRED." Similarly, the occurrence represented by record 472 will expire at 12:29 pm, four minutes from the current date/time. Thus, status field 460 of record 472 is set to "ACTIVE."

Referring now to FIG. 5, there is depicted an exemplary conventional payout table 500. Each record of payout table 500 defines the payout awarded for each outcome, or family of outcomes, based on the number of coins wagered. Payout table 500 includes outcome field 502 representing the outcome or family of outcomes associated with a record. Payout table 500 also includes payout fields 504, 506 and 508 representing the payouts for wagers of one, two and three coins, respectively. For example, if a player wagers one coin on a play that results in an outcome of "BAR/ORANGE/ORANGE," slot machine 300 would provide a payout of ten coins, according to payout field 504 of record 522. If two coins were wagered on a play having the same outcome, slot machine 300 would provide a payout of twenty coins, according to payout field 506 of record 522.

Referring now to FIG. 6, there is depicted a table representing the probability of specific outcomes generated by slot machine 300. Although the present invention does not rely on any specific probability table, the selection of a probability table should be consistent with the requirements and payout amounts of the bonus game of the present invention. Each record of probability table 600 represents an outcome or family of outcomes. Probability table 600 includes an outcome field 602 representing an outcome associated with a record. Probability table 600 further includes random number field 604 and expected hits per cycle field 606. Random number field 604 indicates a range of numbers which, when generated by random number generator 322, result in the associated outcome. For example, random numbers 10131-10330 correspond to outcomes for which the last two symbols are "CHERRY," as illustrated by record 616. Outcomes of "ANY/CHERRY/CHERRY" are expected to occur 200 times per cycle of 10,648 total plays in the cycle.

Referring now to FIG. 7, there is depicted outcome table 700 of slot machine 300. Each record of outcome table 300 represents an outcome generated by a play of slot machine 300. Although outcome table 700 may store every outcome from every session, in the illustrated embodiment, outcome table 700 stores the outcomes from every play of a current session. Outcome table 700 includes outcome identifier 702 that functions as a record identifier. Outcome table 700 also includes fields 704, 706 and 708 that represent the symbols from reel 1, reel 2 and reel 3, respectively, which together form the outcome.

Figure 8:
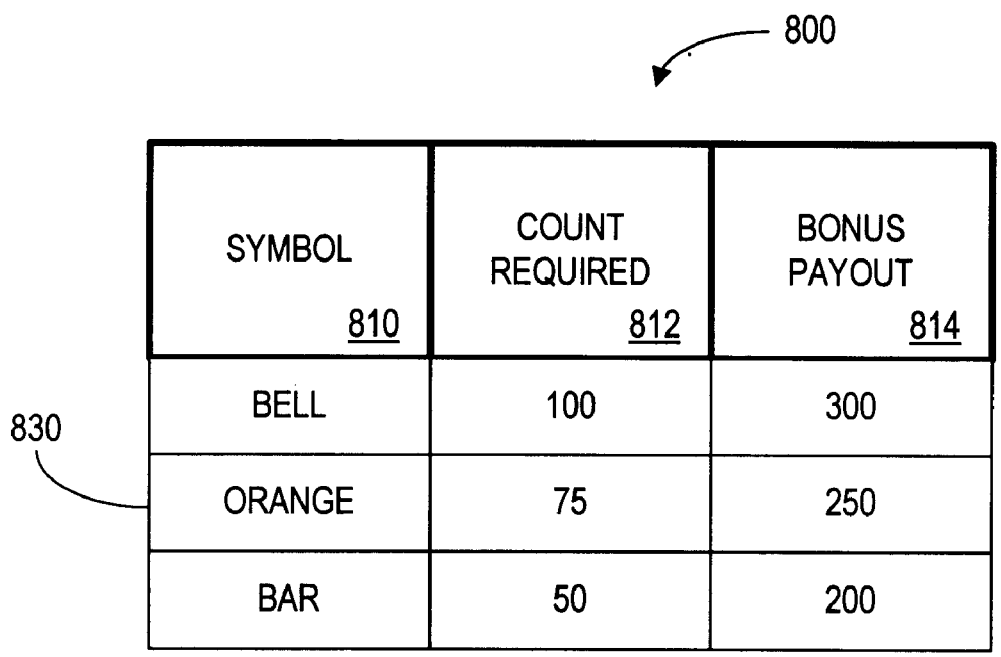
FIG. 8 is a table showing components of the tracked symbol reward table of FIG. 3.

Referring now to FIG. 8, there is depicted tracked symbol reward table 800 of slot machine 300. Each record of table 800 represents a bonus payout and the requirements for achieving the bonus payout. Table 800 includes symbol field 810 and count required field 812. Symbol field 810 and count required field 812 define the requirements for achieving a bonus payout associated with a record. Bonus payout field 814 defines the amount of the bonus payout awarded to a player who achieves the associated requirements.

Description of the Operation

Figure 9A:
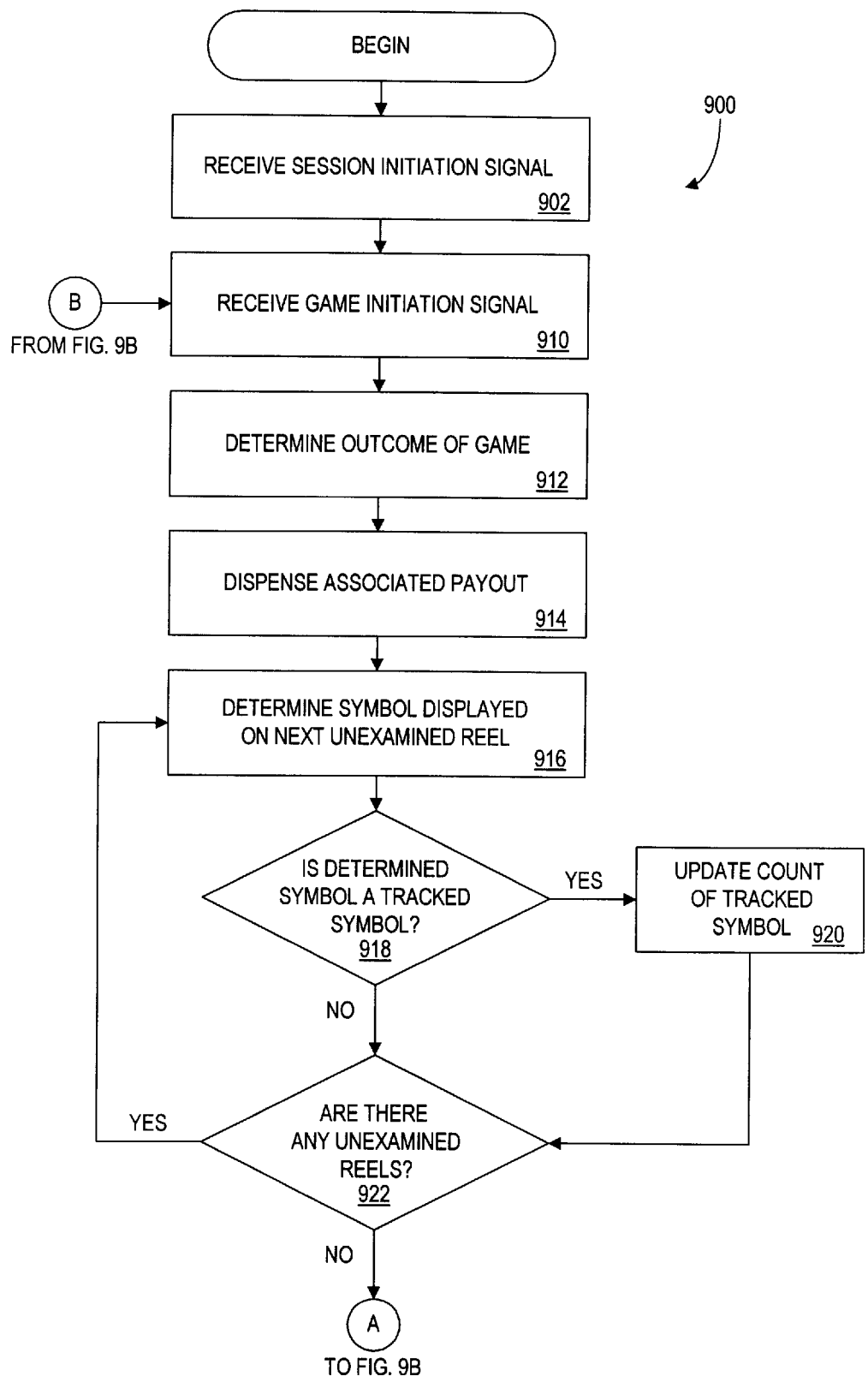
FIGS. 9A–9B together comprise a flowchart illustrating a method for directing a slot machine to determine a bonus payout according to one embodiment of the present invention.
Figure 9B:
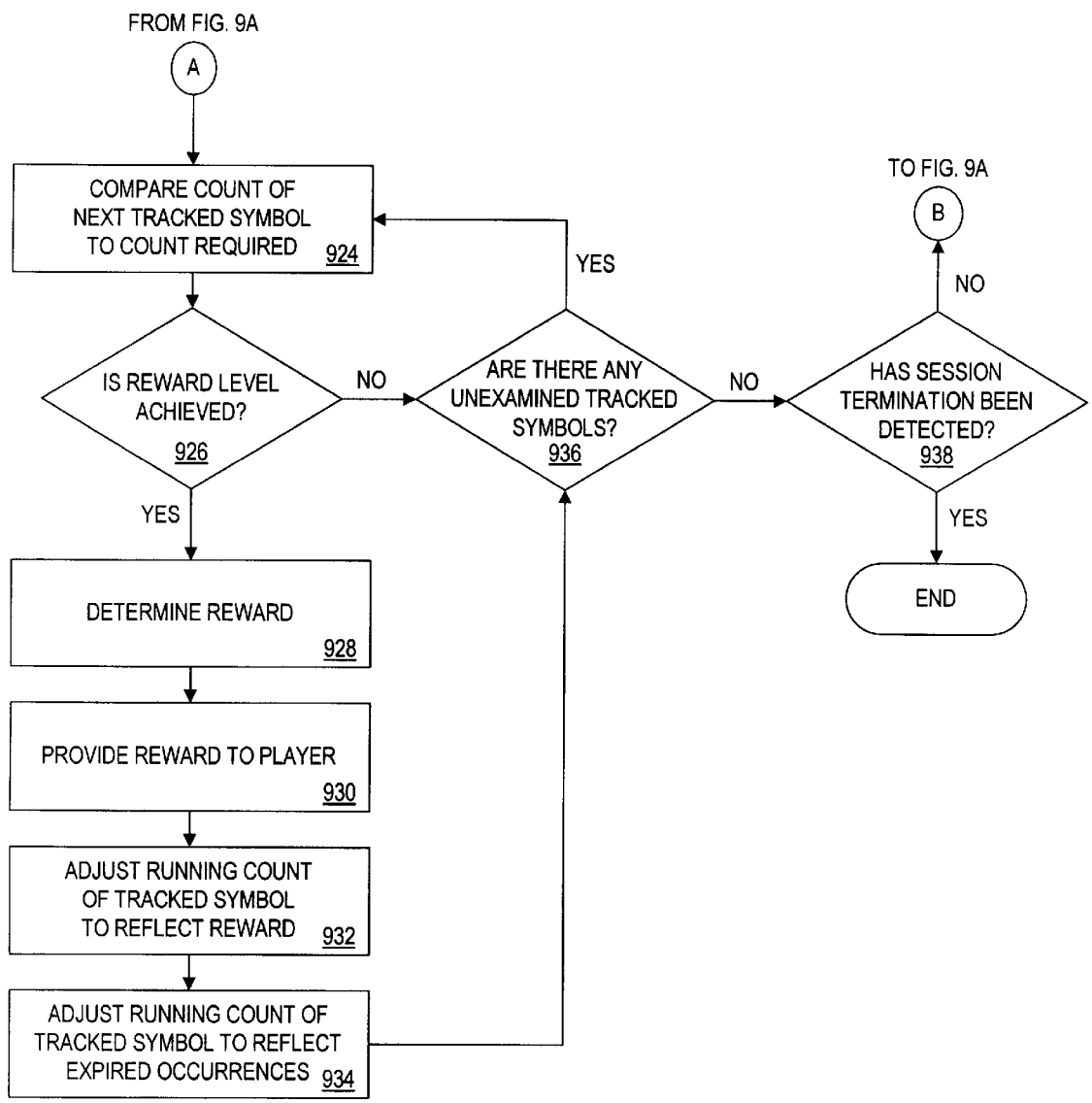

Having thus described the architecture and components of the slot network and slot machines of the preferred embodiment, the operation of the apparatus will now be described in greater detail with reference to FIGS. 9A and 9B. Taken together, FIGS. 9A and 9B depict a flowchart of an exemplary process 900 employed by slot machine 300 to determine a bonus payout according to the present invention. The process steps are implemented using the instructions of program 306.

The process begins with step 902 in which processor 302 receives a signal to initiate a session. Such a signal could be generated as a result of a player inserting a player tracking card. The session initiation signal could also be generated based on insertion of currency after an extended period during which the slot machine was not used. The session initiation signal represents the beginning of a new session.

The process continues with step 910 which directs processor 302 to receives a signal to initiate game play, such as by a pull of handle 350. At step 912, processor 302 determines an outcome for the game and provides the player a payout associated with the outcome, as shown by step 914. Steps 910–914 are game play steps which may be performed in conjunction with certain operating system and control software (not shown) to conduct the primary game offered by slot machine 300.

Steps 916 through 922 define a logical loop that causes each reel of the slot machine to be examined to determine whether the outcome includes any tracked symbols. At step 916, processor 302 determines which symbol is on the next reel that has not been examined. The first time through the loop, the first reel 326 is considered the next reel that has not been examined. Step 918 directs the flow of processing based on whether the determined symbol is a symbol which is tracked for the purpose of awarding a bonus payout. If the determined symbol is a tracked symbol, processor 302 is directed to update the running count of the tracked symbol. Otherwise, processor 302 determines whether all of the reels have been examined, and causes the process flow to loop back to step 916, accordingly.

Referring now to FIG. 9B, steps 924 through 936 define a logical loop that causes processor 302 to examine the running count of each tracked symbol to determine whether a reward level has been achieved. At step 924, the running count 412 of a tracked symbol is retrieved from tracked symbol table 400 and compared to the corresponding count required 812 of tracked symbol reward table. As illustrated by step 926, if a reward level has not been achieved, processor 302 is directed to proceed to step 936.

If a reward level has been achieved, processor 302 determines the reward at step 928 and provides the reward to the player at step 930. The reward is determined by retrieving the corresponding bonus payout 814 from tracked symbol reward table 800. The reward may be provided to the player in a number of ways, including dispensing coins, updating a credit meter, or crediting an account of the player based on identifying information stored on a player tracking card.

At step 932, processor 302 adjusts the running count of the tracked symbol to reflect the reward. In its simplest form, step 932 includes subtracting the count required to achieve the reward from the corresponding running count. Alternately, step 932 could include setting the running count to zero, or in an embodiment in which each occurrence is individually tracked, step 932 would include updating the table of occurrences 450. At step 934, processor 302 is directed to adjust the running count of the tracked symbol to reflect expired occurrences. At step 936, processor 302 is directed to continue examining tracked symbols until all tracked symbols have been examined.

At step 938, processor 302 determines whether the session has been terminated. If the session has not been terminated, process flow is directed back to step 910. Otherwise, the process concludes. The determination of whether a session has been terminated may be made in any number of ways, including detecting the removal of a player tracking card from player tracking device 338. Alternatively, slot machine 300 may determine that a session has been terminated after an extended period of inactivity.

Expiration of Tracked Symbols

Many variations of the present invention are possible. According to the present invention, each occurrence of a tracked symbol has an associated expiration criterion. As described, each accumulated tracked symbols expire after a predetermined time. Of course, the present invention supports accumulated tracked symbols that expire after a predetermined number of plays. For example, after 100 plays, a bell symbol expires. In either event, players are able to accumulate a lot of tracked symbols early in a session providing the appearance that a large jackpot is readily attainable. Late in a session, the occurrences expire at a rate nearly equal to the rate of tracked symbol acquisition, giving the impression that the player is close to winning. This increases the anticipation and excitement of the game because the player feels like he is constantly on the verge of a bonus payout. In either embodiment, the time remaining or plays remaining could be recorded in association with each accumulated occurrence of a tracked symbol. An advantage of a time-based embodiment is that it encourages players to play quickly. Although fast players will tend to win more bonuses, they will also tend to spend more money playing the slot machine.

Storage of Running Counts

Although the present invention, as described, stores running counts locally at the slot machine, the running counts could be associated with a player identifier from a player tracking card and stored by server 200 to allow a player to "carry" the running counts from slot machine to slot machine. Occurrences of tracked symbols stored with the server might expire after a number of hours or days. Such an embodiment also enables a player to end a playing session, save the running counts, and return to the same machine at a later time to resume the game using the stored running counts.

Alternatively, the running counts of accumulated tracked symbols could be stored on the player's tracking card. Such an embodiment would also allow a player to carry running counts from slot machine to slot machine. Any existing running counts would be stored on a player's tracking card at the end of a playing session. The running counts would be read off the card by the next slot machine into which the tracking card is inserted. That machine's running counts would be adjusted accordingly. This embodiment requires that the player card have data storage capability, such as that found in a smart card or writable magnetic strip.

Alternate Rewards

In addition to variations in the expiration of accumulated tracked symbols, variations in determining a bonus payout are also possible. Specifically, the determination of a bonus payout could be based on how many spins or how much time it took to achieve the reward level. For example, the bonus payout for accumulating 100 oranges may be 350 coins if they are accumulated within 30 spins, 325 coins if they are accumulated within 40 spins, and 300 coins if they are accumulated within 50 spins.

Alternatively, the reward provided to a player for attaining a particular reward level might be a payout multiplier instead of coins. For example, upon reaching 50 oranges, the player might earn a ten times multiplier for "ORANGE/ORANGE/ORANGE" enabled for the next 100 handle pulls. In yet another embodiment, slot club reward points could be awarded in place of currency.

Rewards could also be provided for expiring occurrences of tracked symbols. For example, every time a tracked symbol expires (i.e. is deducted from the running count), the player would be awarded a slot club reward point, a percentage of a slot club reward point or a cash-back reward (e.g. $0.01). The reward point or cash-back could then be used in the casino restaurants and/or shops. This extra reward would make the gaming experience more enjoyable by rewarding the player for events that would otherwise be considered "non-winning" events during slot play. The reward point or cash-back earned by the player would be tracked through the player's tracking card in a conventional manner.

Group/Team Play

Although the described embodiment is directed toward individual play, it should be understood that an alternate embodiment of the present invention could support group play. Players could form teams, pooling their accumulated tracked symbols into running counts corresponding to the team. Once the once a reward level is achieved by the team, each team member would be provided a share of the associated bonus. A team may be formed interactively by allowing the player to actuate a "Team Play" button on the gaming device (not shown). Server 200 would link the player to at least one other player in response to the signal resulting from the actuated "Team Play" button.

Alternatively, players may form teams by registering at a kiosk or casino slot club center. In such an embodiment, the player identifiers of the team members would be stored in association with one another and a team identifier in a registration table. The registration table would be accessed when a team member inserts his tracking card into the card reader of a slot machine. The slot would read the player identifier from the player tracking card and transmit it to the server. The server would determine whether the player is registered on a team and, if so, would retrieve the team record in order to update any symbols accumulated by the player into the running counts of the team.

Rules Variations

The slot machine of the present invention could also include program steps for alternate rules. Specifically, each tracked reel symbols could be associated with a particular reel. For example, on a three reel machine, only bars occurring on the first reel would be accumulated, only bells appearing on a the second reel would be accumulated and only oranges appearing on the third reel would be accumulated. A tracked symbol meter could be disposed above each reel for visual association.

Other variations of the disclosed embodiment are also envisioned. Specifically, an alternative embodiment of the present invention could require that a tracked symbol only counts towards the running count if it is not part of a winning combination. Since the present invention is directed toward rewarding players in some way even when their outcome is not a winning one, it is not strictly necessary to reward players a second time for a winning outcome to achieve the objects, features and advantages of the present invention. For example, if bars, bells, and oranges are tracked symbols, and the player receives an outcome of CHERRY-CHERRY-ORANGE, he receives a payout of five coins for every coin wagered in accordance with a conventional payout schedule. Employing the alternate embodiment of the present invention, the player would receive the payout of five coins (if he only wagered one coin) and the orange that is part of that outcome would not be added to the running count of oranges.

Other variations in the rules are also possible. For example, the rules could be altered to adjust the running count only if the player has wagered the maximum amount allowable. Another variation of the rules may enable a player to receive credit for an occurrence of a tracked symbol, even if it is not part of an outcome. Specifically, symbols that are not on the payline but appear on the screen of the slot machine count towards the running count. For example, if an orange is just above or below the payline and oranges are tracked symbols, the running count for oranges would be adjusted.

Another variation of the rules includes cancellation of symbols. In this embodiment, one type of reel symbol may cancel another. In other words, one type of reel symbol may decrease the running count of another reel symbol. For example, a cherry may cancel an orange. Accordingly, if an orange is a tracked symbol, and the running count of oranges is twenty. A player receiving an outcome of CHERRY-7-7 would find his orange balance decreased by one to nineteen.

Yet another variation of the rules includes providing a bonus payout for achieving a certain combination of tracked symbols. For example, a bonus payout of fifty coins could be awarded if each of the running counts is equal to ten simultaneously. In another example, a bonus payout of fifty coins could be awarded if a specific running count exactly matched a required count. The particular number that the running counts would have to equal could be determined by the casino or selected by the player using the keypad 342.

Still another variation of the rules includes displaying special offers to the player upon achieving a predetermined reward level. Such offers could include a free night's stay at the casino hotel, a ticket to a show or other casino event or a free dinner at the casino restaurant. The offers could be determined by the server and be based on revenue-management rules in order to optimize the revenue of the casino. For example, a show starting in a couple of hours may have a large number of empty seats which the casino would rather give away than have them remain empty. The server may determine these offers by checking databases of reservations for the casino hotel or show. The offers may be made upon achieving the predetermined reward level (e.g. "Collect 50 Plums to Win a Free Room!") in place of the monetary award. Alternately, the reward offers could be made when the player is close to achieving the sought after balance (e.g. has 48 plums accumulated). Depending on the reward, it may be more cost effective for the casino to make the offer rather than pay a monetary reward to the player if he does get to the sought after level. If the player accepts the offer, his balance would be reset to zero.

Video Poker Embodiment

The present invention and many of the disclosed variations thereon may be applied to video poker, as well as to slot machines. As in the slot machine embodiments, in a video poker embodiment, a player achieves a running count to earn a reward. The running count is preferably a count of occurrences of types of cards. A type of card may be a specific card value (e.g., aces, twos and threes), a set of card values (e.g., face cards) or a particular suit (e.g., hearts, diamonds, spades and clubs).

In the case where the tracked card types are suits, an exemplary video poker tracked symbol reward table is illustrated as Table I below. Of course, the expiring nature of the card types would apply in the same ways as described with respect to the slot machine embodiments.

TABLE I

Video Poker Tracked Symbol Reward Table

| Suit | Count Required | Bonus Payout |
| --- | --- | --- |
| Hearts | 100 | 200 |
| Clubs | 150 | 250 |

In an alternate embodiment, a running count may be adjusted based on the numeric card values (e.g., face cards are valued at ten, aces are valued at eleven). Regardless of what a running count represents, there are many variations regarding how to adjust the running count in a video poker embodiment. Specifically, there are several ways to determine whether an occurrence of a card type has been generated.

For example, all cards displayed during a game (including discarded cards) could be examined to determine whether a card type occurrence has been generated. In other words, every card displayed during a game is considered in the decision to adjust the running count. In an alternate embodiment, the cards examined to determine whether a card type occurrence has been generated may be limited to only the cards of the final outcome. In such an embodiment, only the cards comprising the final hand are considered in the decision to adjust the running count. In yet another embodiment, only certain card positions may be examined to determine whether an occurrence of a card type has been generated. For example, only the cards displayed in the first card position might be considered in the decision to adjust the running count. Of course, other ways to determine occurrences of tracked symbols in a video poker embodiment are also possible, such as by examining only discarded cards.

While the best mode for carrying out the invention has been described in detail, those familiar with the art to which the invention relates will recognize various alternative designs and embodiments for practicing the invention. These alternative embodiments are within the scope of the present invention. Accordingly, the scope of the present invention embodies the scope of the claims appended hereto.

What is claimed is:

1. A method for directing the operation of a slot machine, the method comprising the steps of:

identifying at least one tracked symbol;

initializing a running count;

generating an outcome represented by a plurality of symbols;

determining an occurrence of the at least one tracked symbol;

adjusting the running count, including increasing the running count to reflect occurrences of the at least one tracked symbol and decreasing the running count to reflect expiration of occurrences of the at least one tracked symbol; and determining a bonus payout based on the running count.

2. The method of claim 1 wherein:

the step of adjusting includes adding a predetermined integer value to the running count; and the step of adjusting further includes subtracting a predetermined integer value from the running count.

3. The method of claim 1 further including the steps of:

identifying an expiration condition representing a number of plays after which an occurrence of the at least one tracked symbol expires; and determining an expiration of an occurrence of the at least one tracked symbol based the expiration condition.

4. The method of claim 1 further including the steps of:

identifying an expiration condition representing a time after which an occurrence of the at least one tracked symbol expires; and determining an expiration of an occurrence of the at least one tracked symbol based on the expiration condition.

5. The method of claim 1 further including the steps of:

determining a payout based on the outcome;

determining whether the payout equals zero; and wherein the step of determining an occurrence is performed only if the payout equals zero.

6. The method of claim 1 further including the step of storing the running count on a player tracking card, and wherein the running count includes status data representing an expiration condition of each occurrence of the at least one tracked symbol.

7. The method of claim 1 further including the step of storing the running count at a slot server, and wherein the running count includes status data representing an expiration criterion of each occurrence of the at least one tracked symbol.

8. The method of claim 1 wherein the step of determining a bonus further includes determining the bonus based on a number of plays of the slot machine.

9. The method of claim 1 wherein the step of determining a bonus further includes determining the bonus based on a duration of time.

10. The method of claim 1 wherein the running count represents occurrences of the at least one tracked symbol generated by a second slot machine.

11. The method of claim 1 further including the step of receiving a wager; and wherein the step of determining a bonus further includes determining the bonus based on a wager amount.

12. The method of claim 1 wherein the at least one tracked symbol includes:

at least one bonus symbol which contributes to the running count;

at least one offsetting symbol; and the step of adjusting the running count further includes subtracting occurrences of the at least one offsetting symbol.

13. The method of claim 1 further including the step of determining a payout, and the step of determining a bonus comprises determining a multiplier to be applied to the payout.

14. The method of claim 1 wherein the step of determining a bonus payout includes determining points for a slot play reward system.

15. The method of claim 14 further including the step of determining a payout for expired occurrences of the at least one tracked symbol.

16. The method of claim 1 wherein the slot machine comprises a reel slot machine, and the symbols comprise reel symbols.

17. The method of claim 16 wherein:

the reel slot machine includes a symbol display window and a payout line visible within the symbol display window; and the step of determining an occurrence includes selecting at least one tracked symbol from amongst all symbols displayed in the symbol display window.

18. The method of claim 16 wherein the step of determining an occurrence includes selecting the at least one tracked symbol from amongst symbols on one specified reel of the reel slot machine.

19. The method of claim 1 wherein the slot machine comprises a video poker machine, and the symbols comprise playing card attributes.

20. The method of claim 19 wherein the at least one tracked symbol comprises a function of the face value of cards dealt in a hand.

21. A method for directing the operation of a slot machine, the method comprising the steps of:

identifying at least one tracked symbol;

associating a predetermined expiration condition with each occurrence of the at least one tracked symbol after which each occurrence of the at least one tracked symbol is expired;

generating a running count including adding new occurrences of the at least one tracked symbol and subtracting expired occurrences of the at least one tracked symbol; and identifying a bonus payout based on the running count.

22. A method for directing the operation of a slot machine, the method comprising the steps of:

identifying at least one tracked symbol having associated therewith an expiration condition after which the at least one tracked symbol is expired;

generating a running count including adding new occurrences of the at least one tracked symbol and subtracting expired occurrences of the at least one tracked symbol, thereby determining an ongoing count of active occurrences of the at least one tracked symbol;

identifying a bonus value; and generating a bonus payout when the running count exceeds the bonus value.

23. A method in accordance with claim 22 wherein the step of generating a running count further includes the steps of:

initializing the running count upon the initiation of a session of play by a player; and terminating the running count upon the termination of the session of play by the player;

whereby the running count is active throughout the session of play.

24. A method for directing the operation of a slot machine, the method comprising the steps of:

initiating a session of play;

identifying at least one tracked symbol;

associating an expiration condition with the at least one tracked symbol after which the at least one tracked symbol is expired;

identifying a bonus value;

accumulating a count of active occurrences of the at least one tracked symbol during the session of play; and awarding a bonus payout when the running count exceeds the bonus value.

25. A slot machine for determining a bonus payout, the slot machine comprising:

a processor;

a memory connected to the processor storing a program to control the operation of the processor;

the processor operative with the program in the memory to:

identify at least one tracked symbol;

initialize a running count;

generate an outcome represented by a plurality of symbols;

determine an occurrence of the at least one tracked symbol;

adjust the running count, including increasing the running count to reflect occurrences of the at least one tracked symbol and decreasing the running count to reflect expiration of occurrences of the at least one tracked symbol; and determine a bonus payout based on the running count.

26. The slot machine of claim 25 wherein the processor is further operative with the program in the memory to:

identify an expiration condition representing a number of plays after which an occurrence of the at least one tracked symbol expires; and determine an expiration of an occurrence of the at least one tracked symbol based the expiration condition.

27. The slot machine of claim 25 wherein the processor is further operative with the program in the memory to:

identify an expiration condition representing a time after which an occurrence of the at least one tracked symbol expires; and determine an expiration of an occurrence of the at least one tracked symbol based on the expiration condition.

28. The slot machine of claim 25 wherein the processor is further operative with the program in the memory to:

determine a payout based on the outcome;

determine whether the payout equals zero; and wherein an occurrence is determined only if the payout equals zero.

29. The slot machine of claim 25 wherein the processor is further operative with the program in the memory to store the running count on a player tracking card, and wherein the running count includes status data representing an expiration condition of each occurrence of the at least one tracked symbol.

30. The slot machine of claim 25 wherein the processor is further operative with the program in the memory to store the running count at a slot server, and wherein the running count includes status data representing an expiration criterion of each occurrence of the at least one tracked symbol.

31. The slot machine of claim 25 wherein the processor is further operative with the program in the memory to determine the bonus based on a number of plays of the slot machine.

32. The slot machine of claim 25 wherein the processor is further operative with the program in the memory to determine the bonus based on a duration of time.

33. The slot machine of claim 25 wherein the running count represents occurrences of the at least one tracked symbol generated by a second slot machine.

34. The slot machine of claim 25 wherein the processor is further operative with the program in the memory to receive a wager; and wherein the bonus is determined based on a wager amount.

35. The slot machine of claim 25 wherein the processor is further operative with the program in the memory to:

determine a payout, and determine the bonus by determining a multiplier to be applied to the payout.

36. The slot machine of claim 25 wherein the processor is further operative with the program in the memory to determine the bonus payout by determining points for a slot play reward system.

37. The slot machine of claim 36 wherein the processor is further operative with the program in the memory to determine a payout for expired occurrences of the at least one tracked symbol.

38. The slot machine of claim 25 wherein the slot machine comprises a video poker machine, and the symbols comprise playing card attributes.

39. A slot machine for determining a bonus payout, the slot machine comprising:

a processor;

a memory connected to the processor storing a program to control the operation of the processor;

the processor operative with the program in the memory to:

identify at least one tracked symbol;

associate a predetermined expiration condition with each occurrence of the at least one tracked symbol after which each occurrence of the at least one tracked symbol is expired;

generate a running count including adding new occurrences of the at least one tracked symbol and subtracting expired occurrences of the at least one tracked symbol; and identify a bonus payout based on the running count.

40. A slot machine for determining a bonus payout, the slot machine comprising:

a processor;

a memory connected to the processor storing a program to control the operation of the processor;

the processor operative with the program in the memory to:

identify at least one tracked symbol having associated therewith an expiration condition after which the at least one tracked symbol is expired;

generate a running count including adding new occurrences of the at least one tracked symbol and subtracting expired occurrences of the at least one tracked symbol, thereby determining an ongoing count of active occurrences of the at least one tracked symbol;

identify a bonus value; and generate a bonus payout when the running count exceeds the bonus value.

41. A slot machine for determining a bonus payout, the slot machine comprising:

a processor;

a memory connected to the processor storing a program to control the operation of the processor;

the processor operative with the program in the memory to:

initiate a session of play;

identify at least one tracked symbol;

associate an expiration condition with the at least one tracked symbol after which the at least one tracked symbol is expired;

identify a bonus value;

accumulate a count of active occurrences of the at least one tracked symbol during the session of play; and award a bonus payout when the running count exceeds the bonus value.

42. A slot machine for determining a bonus payout, the slot machine comprising:

means for identifying at least one tracked symbol;

means for initializing a running count;

means for generating an outcome represented by a plurality of symbols;

means for determining an occurrence of the at least one tracked symbol;

means for adjusting the running count, including increasing the running count to reflect occurrences of the at least one tracked symbol and decreasing the running count to reflect expiration of occurrences of the at least one tracked symbol; and means for determining a bonus payout based on the running count.

43. A slot machine for determining a bonus payout, the slot machine comprising:

means for identifying at least one tracked symbol;

means for associating a predetermined expiration condition with each occurrence of the at least one tracked symbol after which each occurrence of the at least one tracked symbol is expired;

means for generating a running count including adding new occurrences of the at least one tracked symbol and subtracting expired occurrences of the at least one tracked symbol; and means for identifying a bonus payout based on the running count.

44. A slot machine for determining a bonus payout, the slot machine comprising:

means for identifying at least one tracked symbol having associated therewith an expiration condition after which the at least one tracked symbol is expired;

means for generating a running count including adding new occurrences of the at least one tracked symbol and subtracting expired occurrences of the at least one tracked symbol, thereby determining an ongoing count of active occurrences of the at least one tracked symbol;

means for identifying a bonus value; and means for generating a bonus payout when the running count exceeds the bonus value.

45. A slot machine for determining a bonus payout, the slot machine comprising:

means for initiating a session of play;

means for identifying at least one tracked symbol;

means for associating an expiration condition with the at least one tracked symbol after which the at least one tracked symbol is expired;

means for identifying a bonus value;

means for accumulating a count of active occurrences of the at least one tracked symbol during the session of play; and means for awarding a bonus payout when the running count exceeds the bonus value.

46. A computer-readable storage medium encoded with processing instructions for implementing a method for directing a slot machine to determine a bonus payout, said processing instructions for directing a computer to perform the steps of:

identifying at least one tracked symbol;

initializing a running count;

generating an outcome represented by a plurality of symbols;

determining an occurrence of the at least one tracked symbol;

adjusting the running count, including increasing the running count to reflect occurrences of the at least one tracked symbol and decreasing the running count to reflect expiration of occurrences of the at least one tracked symbol; and determining a bonus payout based on the running count.

47. A computer-readable storage medium encoded with processing instructions for implementing a method for directing a slot machine to determine a bonus payout, said processing instructions for directing a computer to perform the steps of:

identifying at least one tracked symbol;

associating a predetermined expiration condition with each occurrence of the at least one tracked symbol after which each occurrence of the at least one tracked symbol is expired;

generating a running count including adding new occurrences of the at least one tracked symbol and subtracting expired occurrences of the at least one tracked symbol; and identifying a bonus payout based on the running count.

48. A computer-readable storage medium encoded with processing instructions for implementing a method for directing a slot machine to determine a bonus payout, said processing instructions for directing a computer to perform the steps of:

identifying at least one tracked symbol having associated therewith an expiration condition after which the at least one tracked symbol is expired;

generating a running count including adding new occurrences of the at least one tracked symbol and subtracting expired occurrences of the at least one tracked symbol, thereby determining an ongoing count of active occurrences of the at least one tracked symbol;

identifying a bonus value; and generating a bonus payout when the running count exceeds the bonus value.

49. A computer-readable storage medium encoded with processing instructions for implementing a method for directing a slot machine to determine a bonus payout, said processing instructions for directing a computer to perform the steps of:

initiating a session of play;
identifying at least one tracked symbol;
associating an expiration condition with the at least one tracked symbol after which the at least one tracked symbol is expired;
identifying a bonus value;
accumulating a count of active occurrences of the at least one tracked symbol during the session of play; and
awarding a bonus payout when the running count exceeds the bonus value.

* * * * *